(12) United States Patent
Enderle et al.

(10) Patent No.: US 10,624,689 B2
(45) Date of Patent: Apr. 21, 2020

(54) ABLATION DEVICE FOR LARGE-AREA MUCOSAL ABLATION

(71) Applicant: Erbe Elektromedizin GmbH, Tübingen (DE)

(72) Inventors: Markus Enderle, Tübingen (DE); Klaus Fischer, Nagold (DE); Thomas Stäbler, Tübingen (DE)

(73) Assignee: Erbe Elektromedizin GmbH, Tübingen (DE)

(*) Notice: Subject to any disclaimer, the term of this patent is extended or adjusted under 35 U.S.C. 154(b) by 192 days.

(21) Appl. No.: 15/261,392

(22) Filed: Sep. 9, 2016

(65) Prior Publication Data

US 2017/0071653 A1    Mar. 16, 2017

(30) Foreign Application Priority Data

Sep. 10, 2015 (EP) .................................. 15184682

(51) Int. Cl.
*A61B 18/04* (2006.01)
*A61B 18/14* (2006.01)
(Continued)

(52) U.S. Cl.
CPC ........ *A61B 18/042* (2013.01); *A61B 18/1492* (2013.01); *A61B 2017/00477* (2013.01);
(Continued)

(58) Field of Classification Search
CPC .............. A61B 18/042; A61B 18/1492; A61B 2017/00477; A61B 2017/0046;
(Continued)

(56) References Cited

U.S. PATENT DOCUMENTS

| 6,047,700 A | 4/2000 | Eggers et al. |
| 6,336,926 B1 | 1/2002 | Goble |

(Continued)

FOREIGN PATENT DOCUMENTS

| CN | 1336812 A | 2/2002 |
| CN | 1874732 A | 12/2006 |

(Continued)

OTHER PUBLICATIONS

European search report in corresponding European application No. EP 15 18 4682, dated Mar. 2, 2016, 12 pages.

(Continued)

*Primary Examiner* — Jaymi E Della
*Assistant Examiner* — Rachel A. Vierra
(74) *Attorney, Agent, or Firm* — Fitch, Even, Tabin & Flannery LLP (57) ABSTRACT

The ablation device (11) according to the invention is distinguished by a head (20) having a noncircular cross-section and by electrodes (32, 33) being positioned at an acute angle relative to each other. Due to the angular arrangement of the electrodes and the appropriate configuration of the channels (28, 29), there results an approximately fan-shaped plasma beam with which—in particular with the alternating activation of the two electrodes—a wide strip-shaped ablation region can be achieved on hollow organs of living beings. Handling is reliable and simplified, and, compared to existing measures, the treatment time is reduced.

19 Claims, 4 Drawing Sheets

(51) Int. Cl.
*A61B 18/00* (2006.01)
*A61B 17/00* (2006.01)

(52) U.S. Cl.
CPC ............... *A61B 2018/00166* (2013.01); *A61B 2018/00494* (2013.01); *A61B 2018/00577* (2013.01); *A61B 2018/00982* (2013.01)

(58) Field of Classification Search
CPC .......... A61B 2018/00166; A61B 2018/00494; A61B 2018/00577; A61B 2018/00982; A61B 2018/00184; A61B 2018/00202; A61B 18/04; A61B 18/14
See application file for complete search history.

(56) References Cited

U.S. PATENT DOCUMENTS

| | | | | |
|---|---|---|---|---|
| 6,430,426 | B2* | 8/2002 | Avitall | A61B 5/0422 600/374 |
| 7,625,368 | B2* | 12/2009 | Schechter | A61B 18/02 606/21 |
| 7,658,738 | B2* | 2/2010 | Nobis | A61B 1/00073 600/105 |
| 8,641,711 | B2 | 2/2014 | Douglas et al. | |
| 2002/0077585 | A1* | 6/2002 | Sussman | A61F 9/00736 604/22 |
| 2005/0261674 | A1 | 11/2005 | Nobis et al. | |
| 2007/0049925 | A1 | 3/2007 | Phan et al. | |
| 2007/0088344 | A1 | 4/2007 | Schechter et al. | |
| 2008/0243114 | A1 | 10/2008 | Schnitzler | |
| 2009/0069805 | A1* | 3/2009 | Fischer | A61B 17/3203 606/42 |
| 2009/0157114 | A1* | 6/2009 | Fischer | A61B 17/00234 606/192 |
| 2010/0114092 | A1* | 5/2010 | Eisele | A61B 18/042 606/41 |
| 2011/0184408 | A1 | 7/2011 | Konesky et al. | |
| 2012/0029498 | A1 | 2/2012 | Branovan | |
| 2012/0172874 | A1* | 7/2012 | Fischer | A61B 18/042 606/49 |

FOREIGN PATENT DOCUMENTS

| | | |
|---|---|---|
| CN | 101588765 A | 11/2009 |
| CN | 202397597 U | 8/2012 |
| DE | 10000091 A1 | 7/2001 |
| JP | 2002-509756 A | 4/2002 |
| JP | 2006-334398 A | 12/2006 |
| JP | 2007-504900 A | 3/2007 |
| JP | 2010-516362 A | 5/2010 |
| JP | 2013-111308 A | 6/2013 |
| RU | 2499574 C2 | 11/2013 |
| WO | 9949799 A1 | 10/1999 |
| WO | 0009053 A1 | 2/2000 |
| WO | 2008090004 A1 | 7/2008 |
| WO | 2011022069 A2 | 2/2011 |
| WO | 2011056464 A2 | 5/2011 |

OTHER PUBLICATIONS

First Office Action of the Chinese Patent Office and Search Report dated Sep. 4, 2018, for corresponding CN Application No. 201610805223.4 (18 pgs.).

Russian Office Action dated Sep. 25, 2019, in corresponding Russian Application No. 2016136233/14(056908), with English translation (13 pages).

Japanese Notice of Reasons for Refusal dated Jan. 22, 2020, in corresponding Japanese Application No. 2016-172236, with English translation (14 pages).

Russian Office Action dated Feb. 5, 2020, in corresponding Russian Application No. 2016136233/14(056908), with English translation (10 pages).

English translation of the Chinese Search Report dated Jan. 19, 2020, in corresponding Chinese Application No. 201610805223.4 (1 page).

Chinese Third Office Action dated Feb. 6, 2020, in corresponding Chinese Application No. 201610805223.4, with English translation (8 pages).

* cited by examiner

ABLATION DEVICE FOR LARGE-AREA MUCOSAL ABLATION

RELATED APPLICATION(S)

This application claims the benefit of European Patent Application No. 15184682.1 filed Sep. 10, 2015, the contents of which are incorporated herein by reference as if fully rewritten herein.

TECHNICAL FIELD

The invention relates to an ablation device, in particular for mucosal ablation.

BACKGROUND

Therapeutic mucosal ablation, e.g., for tumor ablation or the destruction of cells of the stomach wall that affect eating behavior, advantageously for the reduction of weight, is typically performed by endoscopic intervention, wherein specific probes can be used for ablation.

For example, document WO 2011/022069 A discloses an endoscope with an end cap that is to be placed on the mucosa, and an argon plasma coagulation is performed in its inside space. The cap is to limit the effective region of the argon plasma coagulation and thus define the mucosal coagulation.

From document U.S. Pat. No. 8,641,711 B2 an instrument for the ablation of tissue layers of hollow organs is known, wherein the instrument comprises an electrically active head with electrodes, said head comprising an expandable element in order to position the head of the instrument relative to the opposing tissue wall. This instrument presupposes hollow organs with a limited diameter as is the case, for example, in the intestines.

The large-area mucosal ablation poses particular challenges for the user from the viewpoints of patience and dexterity. This is true, in particular, when flexible instruments intended for general applications such as polypectomy snares or the like are used. With the use of such snares only a resection of the mucosa of approximately 2 cm² is performed in one operating step. In the fundus and cardia region of the stomach, a resection with the aid of a flexible endoscope is very difficult. In addition, there is the risk of perforation.

In mucosal ablation, an insufficient ablation must be rejected as much as an effect that is too deep because, as a result of this, underlying tissue layers could be damaged up to and including the perforation of the stomach.

SUMMARY

Therefore, the object is the wish for an instrument and a method by means of which the mucosal ablation can be performed in the manner of a safe process and, optionally, extending over larger areas and with good quality.

The ablation device in accordance with the invention comprises a head with two channels and with electrodes arranged in said channels. The channels and/or electrodes together include an acute angle. This angle is preferably between 10° and 60°; preferably it is 10° to 30°, further preferably 25°. The channels are gas conducting channels through which a suitable gas such as, for example, argon may be conducted. In doing so, it is possible—with the aid of the sparks emitted by the electrodes—to generate an argon plasma that can be utilized for a coagulation of the tissue located in front of the electrodes. Although the ablation device comprises at least two electrodes, it is preferably a monopolar instrument. This means that the neutral electrode is not provided on the instrument but on a large surface on the patient. Thus, the current flow occurs between the biological tissue and the electrodes of the ablation device.

Due to the arrangement of the channels and/or the arrangement of the electrodes at an acute angle with respect to each other, it can be achieved that the plasma currents discharged by the two channels will diverge and coagulate a wide, strip-shaped region of the mucosa when the ablation device is moved along the mucosa. The plasma jets discharged by the two channels together can form a slightly fan-shaped flow, i.e., a beam having a non-circular (e.g., oval or strip-shaped) cross-section. The discharge openings of the two channels are preferably on a line that is oriented transversely to the direction of movement of the ablation device. If the angle is suitably defined between the two channels and/or between the two electrodes, as well as the discharge rate of the gas from the channels, the amount of gas, as well as the application of electrical power to the two electrodes, it can be achieved that a more uniform—more uniform in the therapeutic sense—depth effect results across the width of the coagulated strip of the mucosa. In doing so, an even and large-area tissue ablation can be achieved.

The concept according to the invention paves the way for the design of a narrow, slim head that is hardly wider or, in the individual case, also potentially narrower than the track of mucosal tissue generated by said head. This, in turn, allows a simplification of handling and the attachment of the ablation device to an endoscope, in particular the attachment of the ablation device to the distal end of the endoscope, as a result of which its channels remain free for additional instruments as well as for the evacuation of smoke. The endoscope, as well as the attached ablation device, may be arranged in a foil tube. This may have two separated lumens, so that the endoscope is guided through one lumen and the ablation device through the second lumen. A guiding element, for example a spiral tube, in which the ablation device may be arranged so that said device can be moved back and forth in the lumen for the ablation device.

The fact that the head of the ablation device can be moved back and forth in axial direction, i.e., in longitudinal direction of the endoscope, facilitates handling in particular during the ablation of tissue layers in large hollow organs such as, for example, the ablation of mucosa in the stomach. For example, the head of the device may be moved out between 0 mm and 100 mm, in which case an extendibility of up to 50 mm is viewed advantageous, and a 30 mm extension length is viewed as optimal.

It is considered particularly advantageous if the head has on its distal end a noncircular cross-section and the socket allocated to it has a corresponding complementary recess into which the head may retract in proximal direction. As a result of this, the rotatability of the head in the socket is restricted. This considerably facilitates handling of the ablation device. In particular, it can be ensured that the head, due to its retraction, is arranged in a specific rotary position which it will also retain after it is being extended. Advantageously, the head—also in moved-out state—may be brought into a desired position by an elevation on the tube at the proximal end of the socket where an appropriate groove is provided therefor.

In addition to one or more gas conducting channels, a fluid conducting channel may also be provided on the head, said fluid conducting channel being disposed for the discharge of a fluid jet, for example a water jet. The mouth of this channel is preferably arranged between the mouths of the gas channels. For example, a fluid jet may be configured with a pressure or flow rate necessary for injection under the mucosa.

Preferably, the gas channels are provided with a ceramic lining. This allows the continuous operation of the ablation device, in particular, for the ablation of larger areas of the mucosa.

The two electrodes are preferably electrically isolated from each other and connected to dedicated supply lines. The two supply lines may have a common gas supply channel or be guided through separate gas supply channels. Preferably, an electrical current is alternately applied to the two electrodes via dedicated lines, as a result of which a particularly uniform ablation effect and a coagulation depth that is uniform measured across the width of the ablation strip can be achieved. This is true, in particular, when a high-frequency voltage in the range of several hundred kHz is alternately applied to the two electrodes, in which case the switching frequency (alternating frequency) between the two electrodes is a few Hz. The power applied to the electrodes may be, for example, between 10 Watts and 200 Watts, for example 80 Watts or 120 Watts. Further details of advantageous embodiments of the invention are the subject matter of the description, the claims or the drawings. They show in:

DETAILED DESCRIPTION

Figure 1:
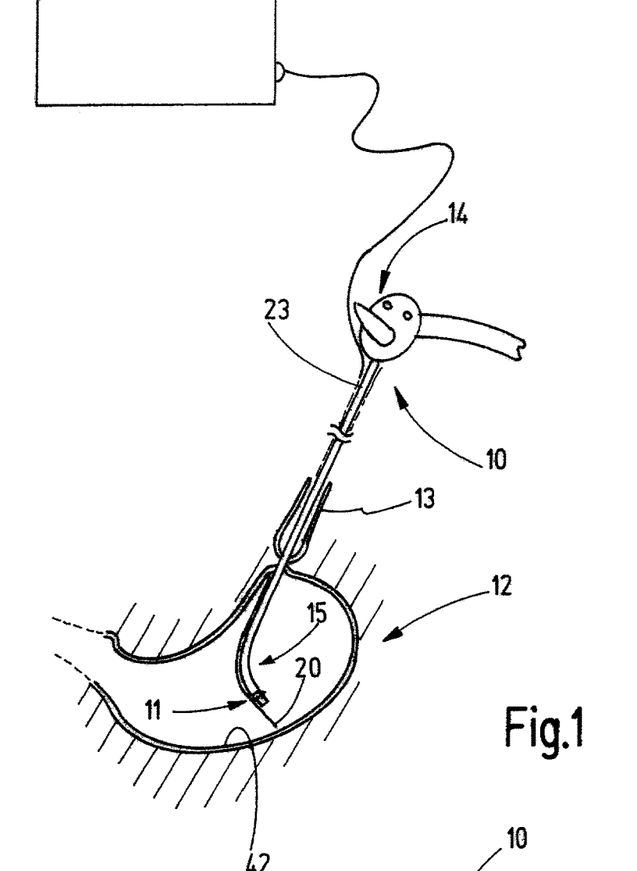
FIG. 1 a schematic illustration of an ablation device according to the invention on the endoscope while in use.

FIG. 1 illustrates the inventive ablation device 11 attached to an endoscope 10 during the procedure of mucosal ablation on a stomach 12. For the procedure, the endoscope 10 and the ablation device 11 are guided through the esophagus 11 13 into the interior of the stomach 12. In so doing, the control elements 14 allow the movement of the endoscope 10, so that, for example, a distal end 15 of the endoscope 10 can curve and/or move along the inner wall of the stomach in a targeted manner, as a result of which various locations of the inside wall of the stomach can be easily reached. The endoscope 10 may contain one or more channels 16 (see FIG. 3a) into which work means such as, for example, surgical instruments can be inserted and by means of which gaseous or liquid fluids can be supplied or discharged. Furthermore, the endoscope 10 may comprise means for image transmission in order to be able to visually control the procedure.

Figure 2:
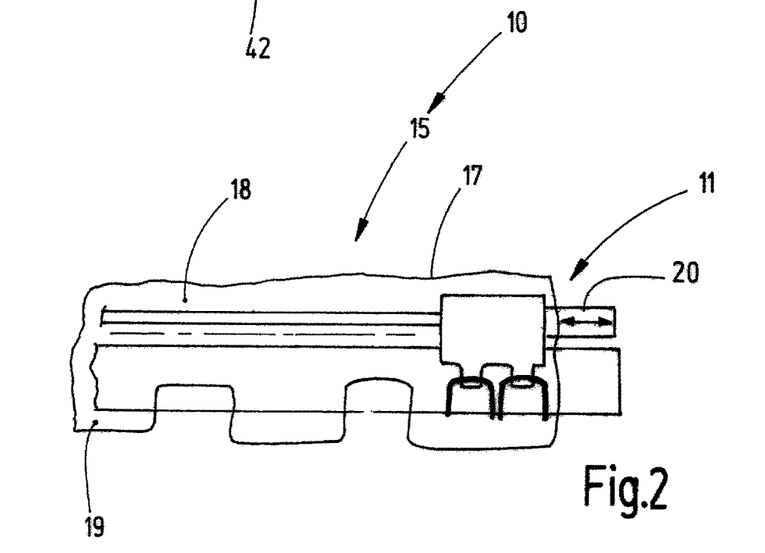
FIG. 2 a section of a side view of one end of an endoscope with the ablation device attached.
Figure 3A:
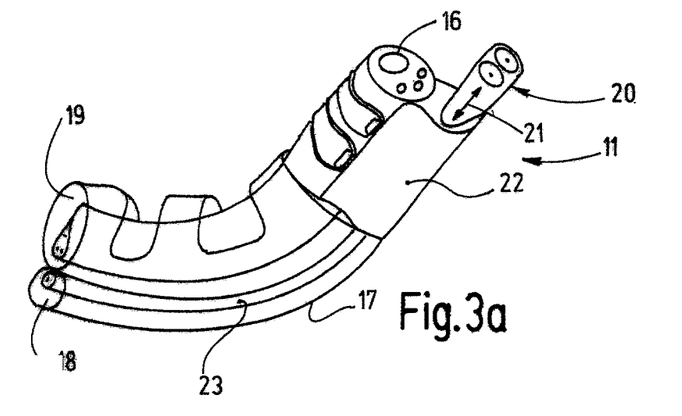
FIGS. 3a/3b/3c a perspective view of the endoscope with the ablation device according to FIG. 2.
Figure 3B:
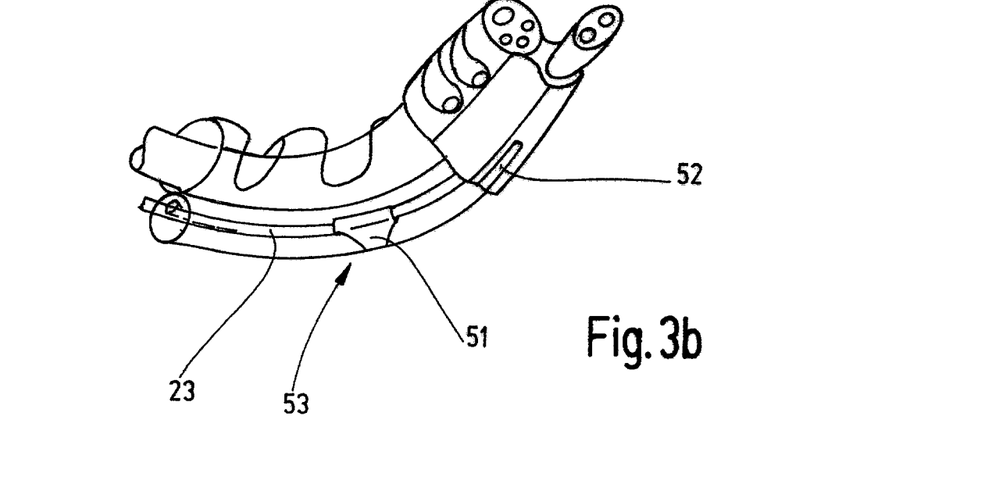
Figure 3C:
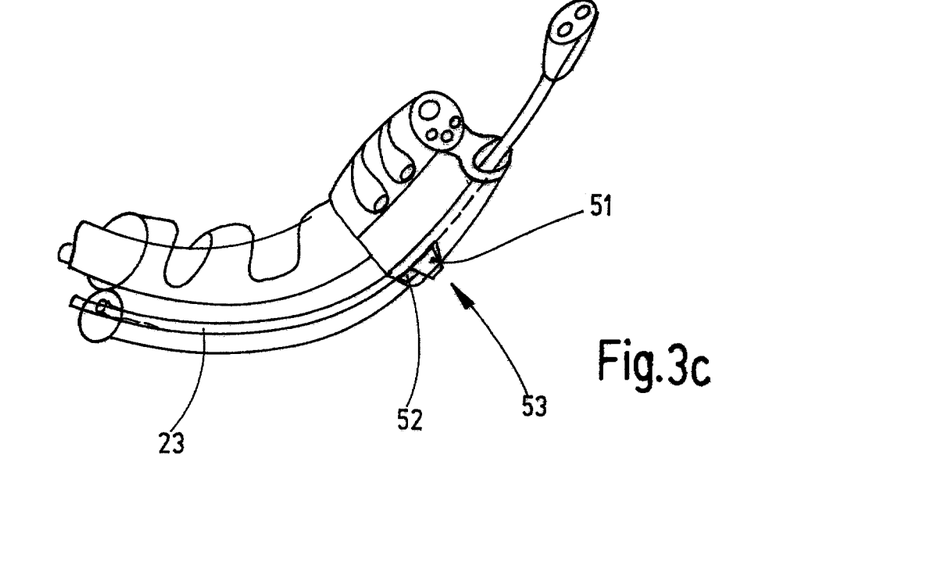
Figure 4:
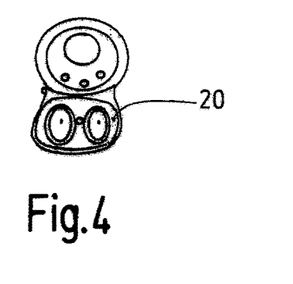
FIG. 4 a front view of the endoscope and the ablation device according to FIGS. 2 and 3.

FIGS. 2 to 4 show the distal end 15 of the endoscope 10 with the ablation device 11 attached thereto. The ablation device, together with the endoscope 10, is arranged in a tube sleeve 17 that contains a first lumen 18 for the ablation device 11 and a second lumen 19 for the endoscope 10. The first and/or the second lumens 18, 19, as is shown by FIGS. 2 and 3, may have slits in order to facilitate bending of the endoscope. The tube sleeve 17 may consist of a thin plastic film that encloses the endoscope 10 and the ablation device 11 with appropriate play.

In the present exemplary embodiment, the ablation device 11 is configured as a device that is attached to the outside of the endoscope 10 and extends along said endoscope. However, the invention is not restricted to this. The ablation device may also be configured as a device that can be guided inside an endoscope. In any event, the device comprises a head 20 that is preferably movably supported, preferably movable in axial direction 21, said direction coinciding with the longitudinal direction of the distal end of the endoscope 10. The head 20 is associated with a socket 22 that is held in or on the endoscope 10. The socket 22 comprises a passage opening into which the head 20 can be moved and through which extends a supply tube 23 for the head 20. Preferably, the supply tube 23 displays tensile stiffness and compressive rigidity, however, it can be easily bent. Therefore, the head 20 can be moved back and forth in axial direction 21 in that the tube 23 is pushed back and forth or pulled accordingly.

Figures 5, 6:
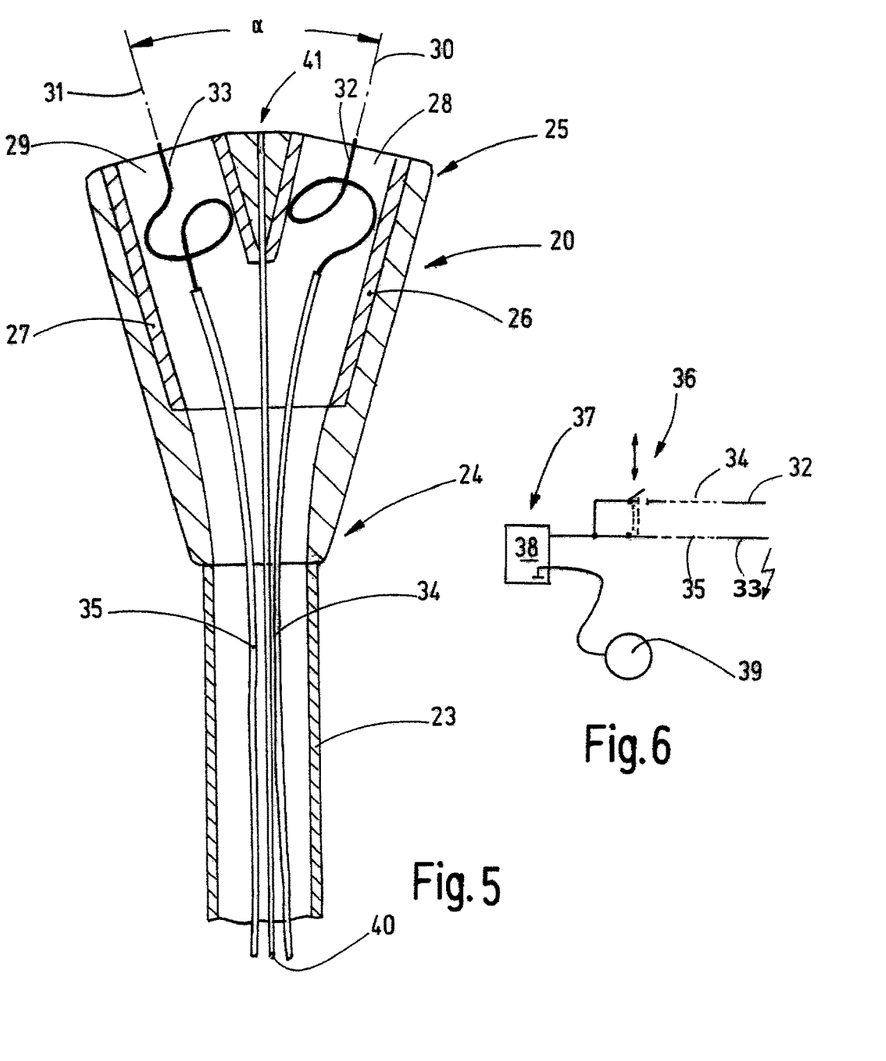
FIG. 5 a sectional view of a detail of the ablation device.
FIG. 6 a circuit diagram of the electrical wiring of the ablation device.

FIG. 4 shows a plan view of the head 20, and FIG. 5 shows it separately in longitudinal section. It is obvious that the head 20 has a cross-section different from the circular form, in particular it has an oval cross-section. In any event, the deviation of the cross-section of the passage opening of the socket 22 and the form of the head 20 are such that the head 20 when retracted finds its way into the passage opening of the socket 22 and, in doing so, rotates into the desired angular position. In order to accomplish this, the head 20 preferably has a circular cross-section on its proximal end 24. At that point, it is configured as a circular cone, for example. Then the cross-section of the cone gradually transitions—starting from the proximal end 24 in the direction of the distal end 25—into the oval form obvious from FIG. 4, in which case the outside surface of the head 20 does not have any offsets that are seated on the mouth of the passage opening of the socket 22, such offsets potentially impairing the retraction of the head 20.

This structural design considerably contributes to the facilitation of handling of the ablation device 11. If the head 20 is pushed far out of the socket 20 so that only the proximal end 24 is still positioned in the socket 22 or that the head 20 is pushed completely out of the socket 22, the head 20 can be rotated by rotating the relatively stiff supply tube 23 into different angular positions. However, if the head 20 is retracted, it finds itself in the socket 22 that then rotates the head 20 into the specified angular position. The movement of the head 20 into the nominal position illustrated by FIGS. 3 and 4 is thus automatically given due to a positive-locking connection between the head 20 and the socket 22. The shape of the head 20 and the socket 22 are adapted to each other in such a manner that the head 20 is fixated in radial direction not only in its end position when it is fully retracted in the socket 22 but essentially maintains this orientation until the head 20 moves completely out of the socket 22. Consequently, it is possible to move the head 20 in axial direction and it will still substantially maintain its rotational orientation. The length of the axial shift, wherein the head 20 substantially maintains its position in radial direction, is 15 mm, preferably 10 mm, particularly preferably 8 mm. The head 20 may be made of a heat-resistant, electrically and thermally poorly conducting material such as, for example, heat-resistant plastic material, Duroplast, ceramic or the like. As indicated in FIG. 5, it is also possible to make the head 20 of plastic material and provide it with ceramic inserts 26, 27 in tubular form, for example. The head may also be entirely made of ceramic.

In order to ensure the orientation of the head 20 in radial direction when the head 20 has been moved in axial direction to such an extent that it moves out of the socket 22, the supply tube 23 may be provided with an anti-rotation lock 53 according to FIGS. 3b and 3c. For this purpose, this anti-rotation lock 53 has a projecting molded lug in the form of a spring 51. This spring 51 engages in a groove provided on the socket 22 and thus secures the head 20 in the desired position in moved-out state (FIG. 3c). The anti-rotation lock 53 may be produced by extrusion-coating with plastic material. The anti-rotation lock 53 may be configured in such a manner that it, together with the socket 22, forms an end stop that delimits the maximum length which the head 20 can be moved in axial direction. It is possible to arrange the anti-rotation lock 53 at a distance from the socket 22 on the supply tube 23, so that, as a result of this, the orientation of rotation of the head 20 is ensured in every axial position. To do so, it is necessary that, just before the head 20 leaves the socket 22, the spring 51 already engages—or at least partially engages—in the groove 52.

It is also possible to arrange the anti-rotation lock 53 in such a manner that the head 20 is held freely movable between its end regions in the direction of rotation. In such an arrangement, the rotation fixation of the head 20 is guaranteed until the head leaves the socket 22 and then again when the spring 51 engages in the groove 52. With a total axial rotation of the head 20 of 50 mm, for example, the fixed direction of rotation of the head 20 may assume approximately 15 mm in the regions of its respective end positions. In between, the head 20 may also be held freely movable approximately 20 mm in radial direction.

The head 20 encloses at least two channels 28, 29 that are disposed to supply gas, in particular inert gas such as, for example, argon to the treatment site. However, also active gasses, aerosols or the like can be supplied, for which purpose the channels 28, 29 may also be used in the same manner. In the present exemplary embodiment, the channels 28, 29 are supplied together with gas via the single supply tube 23. The channels 28, 29 may have a circular cross-section or also cross-sections different therefrom such as an oval cross-section, polygonal cross-sections or the like. On their openings, they have differently oriented opening axes 30, 31 that are indicated by a chain lines in FIG. 5; the opening axes are center axes of the openings of the channels 28, 29 and, together, subtend an angle α that, preferably, ranges between 10° and 60°, preferably between 10° and 30°, and in the preferred case 25°. The channels 28, 29 may also be combined to form one common channels having an oval cross-section or a slit-shaped cross-section, in which both electrodes 32, 33 are arranged.

The distance between the electrodes 32, 33 is preferably several millimeters (3 mm to 12 mm), in which case a distance of 5 mm to 10 mm, in particular 7.5 mm, is advantageous in order to achieve a uniform, wide-stripe tissue ablation with homogeneous ablation depth. The diameter of the electrodes is preferably in the range of 0.2 mm to 1 mm, in which case—in the present exemplary embodiment—a diameter of 0.4 mm has been selected. This has been found to be advantageous due to the high field strengths occurring due to the minimal wire diameter and therefore the good ignition readiness of the electrodes, on the one hand, and the thus attainable tissue effects, on the other hand.

Rod-shaped or needle-shaped electrodes 32, 33 are preferably arranged so as to be centered in the openings of the channels 28, 29, said electrodes being oriented along the opening axes 30, 31. The tips of the electrodes 32, 33 may be located inside the channels 28, 29 or, as indicated in FIG. 5, project from then. The electrodes 32, 33 that, for example, may be made of a heat-resistant metal such as tungsten are retained approximately centered in the channels 28, 29 by a resilient conductor loop as is symbolically indicated in FIG. 5. Connected to the electrodes 32, 33 are supply lines 34, 35 that are electrically insulated with respect to each other and lead through the supply tube 23. As shown in FIG. 6, the lines 34, 35 are connected via a switch arrangement 36 to an electrical power source 37, for example in the form of a high-frequency generator 38. Said generator provides an HF voltage of several hundred kHz (for example, 350 kHz) and a suitable voltage above 1000 V (e.g., 4500 V). The HF generator 38 can apply a power of more than 100 Watts (for example, 120 W).

The voltage is provided with reference to a zero potential to which the patient is connected via at least one neutral electrode 39. This large-area neutral electrode 39 is applied to a suitable part of the body of the patient. The switch arrangement 36 connects the lines 34, 35 and thus the electrodes 32, 33 in an alternating manner, i.e., alternating with the output of the electrical power source 37. The switching frequency with which the electrodes 32, 33 are alternatively activated is in the range of a few Hz, preferably between 1 Hz and 20 Hz, preferably 5 Hz.

In addition, a fluid line 40 may extend through the supply tube 23 and be connected to a nozzle provided on the front side of the head 20. On its distal end, the nozzle has a discharge opening 41 through which a fluid, for example a sodium chloride solution, may be ejected in the form of a jet, for example. With this, it is possible to process the tissue parts, for example, by injection into underlying areas, when the jet exits with corresponding pressure, flow and form so that it may penetrate like a needle into the tissue.

The ablation device 11 that has been described so far operates as follows: The endoscope 10 provided with the ablation device as in FIG. 1 is guided through the esophagus 13 of the patient into the patient's stomach for the planar ablation of the mucosa, for example for the therapeutic treatment of pathological tissue changes, for influencing the weight and eating behavior of patients, or for other therapeutic reasons. By means of control elements 14 of the endoscope 10 the distal end 15 of the latter is positioned at the desired ablation site in such a manner that the tissue site to be treated is within the field of view of the endoscope 10. Now, by appropriate pushing of the supply tube 13, the head 20 of the ablation device 1 is pushed slightly forward so that said tube is positioned at the desired distance from the mucosa 42, for example 3 mm.

Prior to the thermal ablation of the mucosa 42, for example, fluid is introduced into the stomach wall 49 through the discharge opening 41 in such a manner that a fluid cushion is advantageously formed under the desired ablation site. Gas, for example argon, flows through the channels 28, 29. Now the generator 38 and the switch arrangement 36 are activated so that the electrodes 32, 33 will alternately ignite and allow a spark to jump to the mucosa 42. The enveloping argon beam forms a plasma jet 43, 44 in front of each electrode 30, 31, as can be seen in the exemplary embodiment of FIG. 7. In doing so, these jets may combine to form a fan-shaped beam. The plasma jets 43, 44 impinge chronologically offset next to each other on the mucosa 42 and coagulate its uppermost layer, in particular its epithelium 45, as well as the Lamina propria 46 and parts of the submucosa 47. However, the Muscularis propria 48 is preferably spared due to the previously formed fluid cushion.

Due to the alternating energization of the two plasma jets with 5 Hz, a macroscopic combination of the plasma jets 43, 44 takes place. In doing so, a wide tissue strip 50 is coagulated with uniform effective depth. Due to the angular arrangement of the electrodes 32, 33 and the channels 28, 29, the width of the tissue strip 50 may be more than 10 mm, in the individual case approximately 14 mm. The treatment continues in that, by means of the control elements 14 of the endoscope and by appropriate guidance of the supply tube 23, the user moves the head 20 along a path over the mucosa (in FIG. 7, perpendicular to the plane of projection), in which case said head leaves a coagulated strip of tissue having a width of approximately 12 mm to 14 mm. In this manner, the mucosa 42 can be coagulated with great reliability and the reduced risk of damaging the muscularis.

Figure 7:
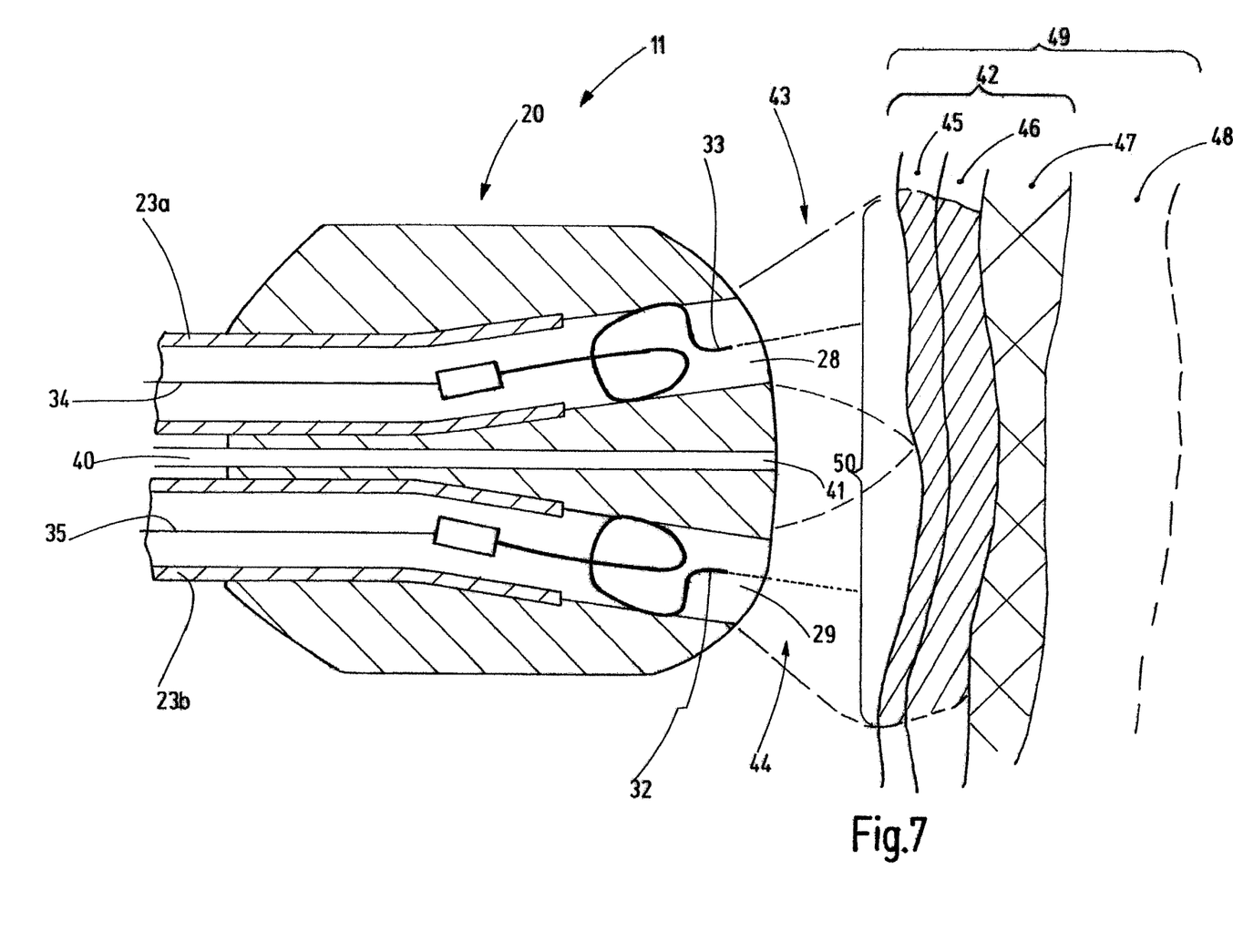
FIG. 7 a schematic representation, in longitudinal section, of a modified embodiment of an ablation device during operation while acting on the mucosa.

FIG. 7 shows a modified embodiment of the ablation device 11. The difference is the configuration of the head 20, the channels 28, 29 of which are supplied by dedicated supply tubes 23a, 23b. Accordingly, the lines 34, 35 can be guided—without separate insulation—in these supply tubes 23a, 23b. Other than that, the description hereinabove applies analogously to this embodiment with the use of the same reference signs.

The ablation device 11 according to the invention is distinguished by a head 20 having a noncircular cross-section and by electrodes 32, 33 being positioned at an acute angle relative to each other. Due to the angular arrangement of the electrodes and the appropriate configuration of the channels 28, 29, there results an approximately fan-shaped plasma beam with which—in particular with the alternating activation of the two electrodes—a wide strip-shaped ablation region (e.g., hollow organs of living beings) can be achieved. Handling is reliable and simplified, and, compared to existing measures, the treatment time is reduced.

| List of Reference Signs: | |
|---|---|
| 10 | Endoscope |
| 11 | Ablation device |
| 12 | Stomach |
| 13 | Esophagus |
| 14 | Control elements |
| 15 | Distal end of the endoscope 10 |
| 16 | Channel of the Endoscope 10 |
| 17 | Tube sleeve |
| 18 | First lumen of the tube sleeve 17 |
| 19 | Second lumen of the tube sleeve 17 |
| 20 | Head |
| 21 | Axial direction |
| 22 | Base |
| 23, 23a, 23b | Supply tube |
| 24 | Proximal end of the head 20 |
| 25 | Distal end of the head 20 |
| 26, 27 | Ceramic inserts |
| 28, 29 | Channels |
| 30, 31 | Opening axes |
| α | Angle between the opening axes 30, 31 |
| 32, 33 | Electrodes |
| 34, 35 | Lines |
| 36 | Switch arrangement |
| 37 | Electrical power source |
| 38 | HF generator |
| 39 | Neutral electrode |
| 40 | Fluid line |
| 41 | Discharge opening |
| 42 | Mucosa |
| 43, 44 | Plasma jet |

| List of Reference Signs: | |
|---|---|
| 45 | Epithelium |
| 46 | Lamina propria |
| 47 | Submucosa |
| 48 | Muscularis propria |
| 49 | Stomach wall |
| 50 | Tissue strip |
| 51 | Molded lug, spring |
| 52 | Groove, slit |
| 53 | Anti-rotation lock |

The invention claimed is:

1. An ablation device comprising:
   a head comprising:
      a first channel with a first electrode arranged at least partially therein, and
      a second channel with a second electrode arranged at least partially therein,
         wherein the first channel and the second channel together, and the first electrode and the second electrode together, define an acute angle (α),
   wherein the first channel and the second channel are configured to eject diverging plasma jets.

2. The ablation device as in claim 1, wherein the first channel and the second channel are gas-conducting channels.

3. The ablation device as in claim 1, wherein the first channel and the second channel both have a rounded mouth with the first electrode and the second electrode centrally placed therein.

4. The ablation device as in claim 1, wherein the first channel and the second channel are made, at least on their distal ends, of a heat-resistant plastic or ceramic material.

5. The ablation device as in claim 1, wherein the first channel and the second channel are connected to a common fluid supply line.

6. The ablation device as in claim 1, wherein the first channel and the second channel are individually connected to dedicated fluid supply lines.

7. The ablation device as in claim 1, wherein an electrical supply line for at least one of the first electrode or the second electrode extends through a fluid supply line.

8. Ablation device as in claim 7, wherein the electrical supply lines (34, 35) of the first electrode and the second electrode (32, 33) are electrically insulated with respect to each other.

9. The ablation device as in claim 1, wherein the head, starting from its distal end, is configured to taper in a proximal direction.

10. The ablation device as in claim 1, wherein the head has a non-circular cross-section on its distal end.

11. The ablation device as in claim 1, wherein the head is associated with a socket with a holding device for attachment to an endoscope, in which case the head can be moved in an axial direction relative to the socket.

12. The ablation device as in claim 11, wherein rotatability of the head in the socket is restricted.

13. The ablation device as in claim 1, wherein a discharge opening for a fluid is arranged on the head.

14. The ablation device as in claim 13, wherein the discharge opening is a nozzle.

15. The ablation device as in claim 13, wherein the discharge opening is arranged so as to be centered between the first electrode and the second electrode.

16. A method for tissue ablation using an ablation device comprising a head comprising a first channel with a first electrode arranged at least partially therein and a second channel with a second electrode arranged at least partially therein, wherein the first channel together, and the first electrode and the second electrode together, define an acute angle ($\alpha$), the method comprising:
   moving the head along a path transversely to a line connecting the first electrode and the second electrode at a distance from a tissue to be ablated, and
   ejecting diverging plasma jets from the first channel and the second channel.

17. The method as in claim 16, further comprising alternatingly applying high frequency (HF) voltage to the first electrode and the second electrode.

18. The method as in claim 16, further comprising, prior to thermal ablation of mucosa by the ablation device, introducing fluid into a stomach wall associated with the mucosa to form a fluid cushion at a desired ablation site.

19. An ablation device comprising:
   a head comprising:
   a first channel with a first electrode arranged at least partially therein, and
   a second channel with a second electrode arranged at least partially therein,
   wherein the first channel and the second channel together, and/or the first electrode and the second electrode together, define an acute angle ($\alpha$);
   wherein the first electrode and the second electrode are both monopolar,
   wherein the first channel and the second channel are configured to eject diverging plasma jets.

* * * * *